United States Patent [19]

Nudelman et al.

[11] 4,229,363
[45] Oct. 21, 1980

[54] 4-HYDROXY-3-(SUBSTITUTEDMETHYL)-BENZENEACETIC ACIDS

[75] Inventors: Abraham Nudelman, Rehovot; Abraham Patchornik, Ness-Ziona, both of Israel

[73] Assignee: Yeda Research and Development Co., Ltd., Rehovot, Israel

[21] Appl. No.: 940,727

[22] Filed: Sep. 7, 1978

Related U.S. Application Data

[63] Continuation-in-part of Ser. No. 858,725, Dec. 8, 1977, abandoned.

[51] Int. Cl.$^2$ ............................................ C07C 161/03
[52] U.S. Cl. ................................ 260/454; 260/239.1; 260/349; 260/453 A; 544/26; 544/27; 544/29; 544/30; 560/75; 562/429; 562/471; 562/477; 562/478; 546/290; 548/351; 548/136; 548/251; 548/263

[58] Field of Search ................ 260/349, 332 A, 454; 544/29, 30; 562/478, 471, 429; 560/75

[56] References Cited

U.S. PATENT DOCUMENTS

| | | | |
|---|---|---|---|
| 3,689,540 | 9/1972 | James et al. | 562/477 |
| 3,758,562 | 9/1973 | Vesley et al. | 562/478 X |
| 3,830,808 | 8/1974 | Clark et al. | 544/30 X |
| 3,919,206 | 11/1975 | Patchornik et al. | 260/332.2 A X |
| 3,919,208 | 11/1975 | Patchornik et al. | 260/332.2 A X |
| 3,985,741 | 10/1976 | Crast, Jr. et al. | 544/30 |
| 4,045,438 | 8/1977 | Haviv et al. | 544/29 |
| 4,053,597 | 10/1977 | Martel et al. | 544/30 X |

*Primary Examiner*—John D. Randolph
*Attorney, Agent, or Firm*—L. Ruth Hattan; George W. Rauchfuss, Jr.; Eugene O. Retter

[57] ABSTRACT

New 4-hydroxy-3-(substitutedmethyl)benzeneacetic acids have been prepared which are useful as starting materials in the preparation of cephalosporin and penicillin derivatives.

9 Claims, No Drawings

4-HYDROXY-3-(SUBSTITUTEDMETHYL)-BENZENEACETIC ACIDS

This application is a continuation-in-part of copending application Ser. No. 858,725 filed December 8, 1977, now abandoned.

FIELD OF THIS INVENTION

This invention relates to novel acetic acid derivatives useful as intermediates in the synthesis of penicillins and cephalosporins, and processes for their preparation.

SUMMARY OF THIS INVENTION

Compounds of Formula 1 are useful in the synthesis of cephalosporin and penicillin derivatives

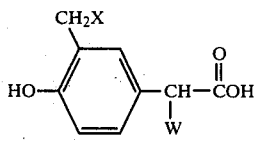

Formula 1 wherein W is hydrogen; hydroxy; —$SO_3H$ or —$COOR_1$ wherein $R_1$ is selected from hydrogen, phenyl or 5-indanyl, or a 1 to 4 carbon alkyl group; —$NHR_2$ wherein $R_2$ is hydrogen, tert-butyloxycarbonyl,

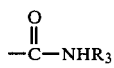

wherein $R_3$ is hydrogen, a lower alkyl group of from 1 to 4 carbon atoms or a phenyl group; X is an alkoxy group of from 1 to 4 carbon atoms; an $R_4$—S— group wherein $R_4$ is a lower alkyl group of from 1 to 4 carbon atoms, azido; NCNH—; $HSO_3$—; —SCN; —OCN; $CH_3SO_2NH$—; thiourea, substituted thiourea wherein the substituents are amino, formylamino, guanylamino, a lower alkyl group of from 1 to 4 carbon atoms and concatenated alkylene groups in the form of a series of from 2 to 6 methylene groups; pyridylthio; 1-methyltetrazol-5-ylthio; 1,3,4-thiadiazol-2-ylthio; 1,3,4-triazol-2-ylthio; —SH; $SSO_3H$; $F_3CS$—;

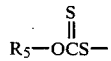

wherein $R_5$ is lower alkyl of from 1 to 4 carbon atoms;

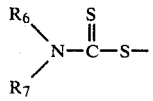

wherein $R_6$ and $R_6$ separately are hydrogen, a lower alkyl group of from 1 to 4 carbon atoms, when taken together $R_6$ and $R_7$ may form a concatenated chain of from 4 to 7 methylene groups, a concatenated chain of from 5 to 7 methylene groups wherein one of these methylene groups is replaced by an oxygen atom or an $R_8$-N group wherein $R_8$ is a lower alkyl group of from 1 to 4 carbon atoms; an $R_4$—SO— group, or an $R_4SO_2$— group.

Within the scope of this invention are included the (—)-isomer, the (+)-isomer or mixtures thereof of compounds of Formula 1 wherein W is other than hydrogen or —COOH. Also included are the acceptable salts of compounds of Formula 1.

DETAILED DESCRIPTION OF THIS INVENTION

Illustrative examples of lower alkyl groups of from 1 to 4 carbon atoms which $R_1$ to $R_8$ inclusive may represent in Formula 1 are methyl, ethyl, propyl, isopropyl, n-butyl, sec-butyl, iso-butyl and tert-butyl. Examples of lower alkoxy groups which X may represent are methoxy, ethoxy, n-propoxy and n-butoxy.

The compounds of Formula 1 wherein X is other than an $R_4SO$— or an $R_4SO_2$— group and $R_2$ is other than tert-butoxycarbonyl may be prepared by the nucleophilic displacement of a halogen atom from a compound of Formula 2 by means of a nucleophile, MZ, as shown in FIG. 1

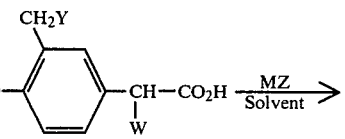

Formula 2        Figure 1

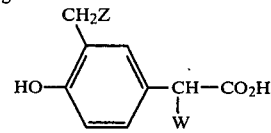

Formula 1

W is as defined in Formula 1 with the proviso that $R_2$ is other than tert-butyloxycarbonyl group. Y represents a halogen such as chlorine or bromine and M represents hydrogen or a cation such as silver, ammonium, an alkali metal or an alkaline earth metal ion such as sodium, potassium or calcium or a pyrrolidinium or morpholinium ion.

The nucleophiles, represented by MZ, are commercially available or may be prepared by standard procedures known in the art. Compounds represented by MZ may be the following: sodium azide, methanol, sodium methoxide, sodium methylthiolate, calcium cyanamide, sodium sulfite, potassium bisulfite, ammonium thiocyanate, silver cyanate, sodium methanesulfonamide, thiourea, thiosemicarbazide, guanylthiourea, ethylene thiourea, formylthiosemicarbazide, silver trifluoromethylthiolate, sodium thiosulfite, 2,3 or 4-mercaptopyridine, sodium sulfide, 1-methyltetrazol-5-ylthiol, 1,3,4-thiadiazol-5-ylthiol, 1,3,4-triazol-2-ylthio, potassium ethylxanthate,

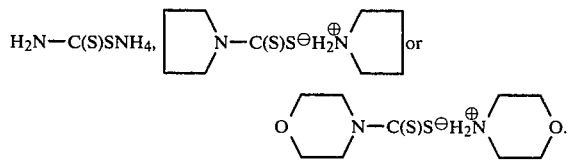

Compounds of Formula 2 may be prepared by the halomethylation of compounds of the Formula 2A, which are commercially available, may be prepared by known methods or are as described herein

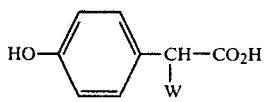
Formula 2A where W is as defined for compounds of Formula 1 with the proviso that $R_2$ is other than tert-butyloxycarbonyl and $R_1$ is hydrogen which comprises reacting equivalent amounts of a compound represented by Formula 2A with formaldehyde in concentrated hydrochloric, hydrobromic, sulfuric, acetic or phosphoric acid, optionally in the presence of a Lewis acid catalyst such as $AlCl_3$, $TiCl_4$, $SnCl_4$ and then adding hydrogen chloride or hydrogen bromide gas to the reaction mixture maintained at about $-10°$ C. to about $100°$ C. for from 30 minutes to 10 hours.

The nucleophilic displacement reaction schematically described in FIG. 1 is carried out in a suitable solvent at temperatures of from $0°$ C. to $100°$ C. for from 0.5 hour to 30 hours at a molar ratio of MZ to Formula 1 compound of from 1 to 1 to 10 to 1.

Suitable solvents for the reaction are, for example, water, methanol, ethanol, propanol, isopropanol, dimethylformamide, dimethylsulfoxide, acetonitrile, acetone and mixtures thereof.

When the reaction hereinabove described in FIG. 1 is carried out under the specified conditions using optically active compounds of Formula 2, the thus produced compounds of Formula 1 show little or no loss of optical purity.

Compounds of Formula 1 where X is an $R_4SO-$ or an $R_4SO_2-$ group may be prepared by the stepwise sulfur-oxidation of compounds of Formula 1 where X is an $R_4S-$ group.

For example, a compound of Formula 1 wherein X is $-SR_4$ in a suitable solvent such as water or water-methanol is reacted with an equimolar amount of an oxidant for 3 to 15 hours at a temperature of from $0°$ C. to $50°$ C.

This stepwise sulfur-oxidation may be carried out by procedures known in the art. For example treatment of a compound of Formula 1 wherein X is $R_4-S-$ with 1 equivalent of sodium metaperiodate (Leonard and Johnson, J. Org. Chem., 27, 282 (1962)), meta-chloroperbenzoic acid (Johnson, et al., J. Org. Chem., 35, 3655 (1970)), $H_2O_2$ (Ogura and Tsuchihashi, Bull. Chem. Soc. Japan, 45, 2203 (1972)), will yield the desired sulfoxide of Formula 1.

Additionally, a compound of Formula 1 wherein X is $R_4S-$ or $R_4SO-$ in a suitable solvent such as water or water-acetic acid may be reacted with an excess (2 to 20 equivalents) of hydrogen peroxide for from 3 to 15 hours at a temperature of from $0°$ to $50°$ C. to give compounds of Formula 1 where X is $R_4SO_2-$.

Acceptable acid addition salts of compounds of this invention include the mineral acid salts, for example, hydrogen chloride, hydrogen bromide, hydrogen iodide, sulfate, sulfamate and phosphate and the organic acid addition salts, such as, maleate, acetate, citrate, oxalate, succinate, malate, mandelate and ascorbate which may be prepared by methods well known in the art.

Acceptable salts may be prepared by reacting compounds of Formula 1 in the acid form with a base by methods well known in the art. The bases may be primary, secondary or tertiary amines such as cyclohexylamine, diethylamine or pyridine or they may include basic compounds of the alkali metal or the alkaline earth metal groups such as sodium bicarbonate, potassium hydroxide, calcium oxide or magnesium hydroxide.

Compounds of Formula 1 wherein $R_1$ is phenyl, 5-indanyl or a 1 to 4 carbon alkyl group may also be prepared by reacting the corresponding monoacid chloride with 5-indanol, a 1 to 4 carbon alcohol, or phenol in a suitable solvent, such as tetrahydrofuran or acetone, containing an acid acceptor such as triethylamine or sodium bicarbonate at a temperature of from about $10°$ to $40°$ C. for from 15 minutes to 2 hours.

Compounds of Formula 1 wherein $R_3$ is hydrogen, a lower alkyl group of from 1 to 4 carbon atoms or a phenyl group may also be prepared from the corresponding amine compound of Formula 1 where $R_2$ is hydrogen. The amine compound may be reacted with cyanic acid, a 1 to 4 carbon alkyl isocyanate or phenyl isocyanate in a suitable solvent such as water containing acetic acid at a temperature of about $10°$ to $30°$ C. for from 1 to 16 hours to give respectively compounds of Formula 1 where $R_3$ is hydrogen, a 1 to 4 carbon alkyl group or a phenyl group.

Compounds of Formula 1 where $R_2$ is a tert-butyloxycarbonyl group may be prepared from the corresponding compounds of Formula 1 where $R_2$ is hydrogen. For example, a compound of Formula 1 wherein $R_2$ is hydrogen may be reacted with a reagent such as tert-butyloxycarbonylazide, 2-(tert-butyloxycarbonyloxyimino)-2-phenylacetonitrile or di-tert-butyldicarbonate at a temperature of from $10°$ to $60°$ C. for from 2 hours to 20 hours in a suitable solvent, for example, water, dioxane, tert-butanol or mixtures thereof and in the presence of a basic material, for example, magnesium oxide, triethylamine or sodium hydroxide; the molar ratio of the compound of Formula 1 to the reagent is from 1 to 1 to 2 to 1.

The acid compounds of the formula

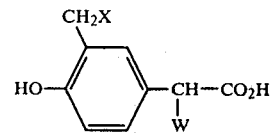

or functional equivalents thereof wherein X is as defined for Formula 1, W is as defined for Formula 1 with the proviso that $R_2$ is other than hydrogen and with the further proviso that when W is hydroxyl, the hydroxyl must be protected, may be coupled with a compound of the formula

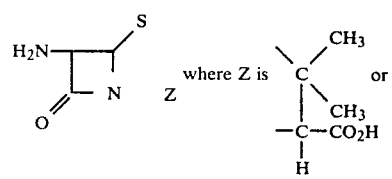

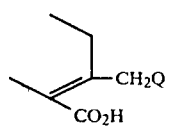

wherein Q is hydrogen, acetyloxy or a heterocyclic thio group such as tetrazol-5-ylthio, 1,3,4-thiadiazol-2-ylthio or 1,2,3-triazol-5-ylthio in a suitable solvent such as tetrahydrofuran, an aliphatic chlorinated hydrocarbon, e.g., methylene chloride, chloroform, water, acetone or mixtures thereof optionally in the presence of an acid acceptor such as triethylamine or sodium bicarbonate at a temperature of from about −10° to about 40° C. for from 30 minutes to 3 hours.

The functional equivalents of the acid compounds include the acid halide, for example, the acid chloride, acid anhydrides, including mixed anhydrides with, for example, alkylphosphoric acid, lower aliphatic monoesters of carbonic acid or aryl sulfonic acids.

Compounds of Formula 1, W is hydroxyl, may be coupled with 7-aminocephalosporin or 6-aminopenicillin derivatives provided that the hydroxyl group is protected. The hydroxyl may be protected by reacting a compound of Formula 1, W is hydroxyl, with bis-(trimethylsilyl)acetamide to form a trimethylsilyl protected hydroxyl group. The trimethylsilyl group is removed during work-up of the coupled product.

A preferred embodiment of this invention are compounds wherein W is amino or tert-butyloxycarbonyl. Compounds wherein X is azido, methyl, thiocyanato, 4,5-dihydro-1H-imidazol-2-ylthio and methylthio are also preferred. Another preferred embodiment of this invention are compounds wherein X is an alkoxy group from 1 to 4 carbon atoms; an $R_4$—S— group wherein $R_4$ is a lower alkyl group of from 1 to 4 carbon atoms; NCNH—; —SCN; —OCN; $CH_3SO_2NH$—; —SH; $SSO_3H$; $F_3CS$—;

wherein $R_5$ is lower alkyl of from 1 to 4 carbon atoms; $R_8$—N wherein $R_8$ is a lower alkyl group of from 1 to 4 carbon atoms; $R_4SO$— or $R_4SO_2$— wherein $R_4$ has the meaning defined hereinabove.

EXAMPLE 1

(−)-α-Amino-3-(chloromethyl)-4-hydroxybenzeneacetic acid hydrochloride

To a solution of (−)-α-amino-4-hydroxybenzeneacetic acid (100 g, 0.6 mole) in a minimum amount of concentrated hydrochloric acid at 35°–40° C. is added 50 ml of aqueous formaldehyde (35–37%) (0.6 mole). The addition of hydrogen chloride gas is begun. After 5–10 minutes, a solid begins to precipitate. Stirring is continued for 30 minutes, and the solid is then collected. The crude product is washed with ether and with acetone. A second crop is obtained from the filtrate after standing at room temperature overnight. Total yield is 102 g (67%) m.p. >300° C., $[\alpha]_D^{18} = -134°$ (c 4.75, $CH_3OH$) NMR (DMSO—$D_6$) ppm (δ) 4.68 (s,2), 4.9 (broad s,1), 6.9–7.6 (superimposed q and s,3).

Anal. calcd for $C_9H_{10}ClNO_3HCl$: Cl 28.13; Found 26.44

In like manner and using equivalent amounts of (−)-α-amino(4-hydroxybenzene)acetic acid, ethyl ester hydrochloride in place of (−)-α-amino(4-hydroxybenzene)acetic acid gives (−)-α-amino(3-chloromethyl-4-hydroxybenzene)-acetic acid, ethyl ester, hydrochloride.

EXAMPLE 2

(−)-α-Amino-3-(bromomethyl)-4-hydroxybenzeneacetic acid hydrobromide

To a solution of (−)-α-amino-4-hydroxybenzeneacetic acid (0.6 mole) in a minimum amount of concentrated hydrobromic acid at 35°–40° C. is added 50 ml of aqueous formaldehyde (35–37%) (0.6 mole). The addition of hydrogen bromide gas is begun. After 5–10 minutes, a solid begins to precipitate. Stirring is continued for 30 minutes. The title compound is collected and washed with ether and acetone.

EXAMPLE 3

3-Chloromethyl-4-hydroxybenzeneacetic acid

4-Hydroxybenzene acetic acid, 0.5 mole, is added to concentrated hydrochloric acid, 50 ml, then 0.5 mole of formaldehyde in the form of a 34–38% solution of formalin is added. Hydrogen chloride is bubbled through the reaction mixture for 60 minutes while maintaining the temperature of the reaction mixture at 35° to 45° C. The reaction mixture is poured into water and the title compound is extracted from the aqueous solution with ethyl acetate. The ethyl acetate is dried over magnesium sulfate, filtered and removed to give the title compound.

EXAMPLE 4

α-Hydroxy-3-(bromomethyl)-4-hydroxybenzeneacetic acid

About 0.3 mole of α-hydroxy(4-hydroxybenzene)acetic acid is added to about 50 ml of concentrated hydrobromic acid containing about 0.1 mole trioxane. The temperature is maintained between about 35° to about 45° C. while passing hydrogen bromide gas through the reaction mixture. After about 90 minutes, the reaction mixture is poured into cold water and the title compound is extracted with ethyl acetate. After drying the organic extract over magnesium sulfate and filtering to remove the magnesium sulfate, removal of the ethyl acetate gives the title compound.

EXAMPLE 5

α-Carboxy-3-(bromomethyl)-4-hydroxybenzeneacetic acid

About 0.5 mole of 4-hydroxybenzeneacetic acid is dissolved in about 50 ml of anhydrous tetrahydrofuran at −40° C. To this solution is added 3 equivalents of lithium diisopropylamide. The temperature is maintained at about −40° C. for about 15 minutes. Then 1 equivalent of ethyl chloroformate is added and the temperature is raised from about −40° C. to about 20° C. and the reaction mixture stirred for about 60 minutes. The reaction mixture is poured into water and the monoester of α-carboxy-4-hydroxybenzeneacetic acid is recovered from the aqueous solution. Hydrolysis of the half-ester with sodium hydroxide followed by acidification with hydrochloric acid gives α-carboxy-4-hydroxybenzeneacetic acid.

α-Carboxy-4-hydroxybenzeneacetic acid, 0.3 mole, is added to aqueous acetic acid (50%) which contains 0.3 mole of chloromethyl methyl ether and a catalytic amount of zinc chloride. The temperature is maintained between about 35° to 45° C. for about 2 hours while hydrogen chloride gas is bubbled through the solution. The reaction mixture is then added to water and the reaction product is recovered by extraction with methylene chloride. After drying the methylene chloride over magnesium sulfate, the magnesium sulfate is removed by filtration. Removal of the methylene chloride gives the title compound.

EXAMPLE 6

α-Sulfo-3-(chloromethyl)-4-hydroxybenzeneacetic acid

Approximately 0.6 mole of 4-hydroxybenzeneacetic acid is added to about 0.9 mole of dioxane-SO$_3$ complex in ethylene chloride maintained at room temperature. This mixture is then stirred at room temperature for 16 hours. The reaction mixture is poured into water and the α-sulfo-(4-hydroxybenzene)acetic acid is recovered from the aqueous solution by evaporation of the dioxane and ethylene chloride.

α-Sulfo-4-hydroxybenzeneacetic acid, 0.3 mole, is dissolved in aqueous sulfuric acid (50%). One equivalent of dichloromethyl ether is added to the solution maintained at between 35° to 45° C. Hydrogen chloride is then bubbled through this reaction mixture for 3 hours. The desired compound is recovered by pouring the reaction mixture into water and extracting the title compound with ethyl acetate. The ethyl acetate is dried over magnesium sulfate. The magnesium sulfate is removed by filtration and evaporation of the ethyl acetate gives the desired compound.

EXAMPLE 7

α-(Aminocarbonyl)amino-3-(chloromethyl)-4-hydroxybenzeneacetic acid

To about 0.15 mole of α-amino-4-hydroxybenzeneacetic acid dissolved in 700 ml of water and 0.2 mole of glacial acetic acid is added about 0.2 mole of potassium cyanate. The resulting mixture is stirred at room temperature for about 30 minutes. The reaction mixture is saturated with sodium chloride and then extracted with ethyl acetate. The ethyl acetate is washed with water, dried over magnesium sulfate, filtered and evaporated to give α-(aminocarbonyl)amino-4-hydroxybenzeneacetic acid Equivalent amounts (0.1 mole) of α-(aminocarbonyl)-amino-4-hydroxybenzeneacetic acid and formaldehyde as a 34-38% formalin solution are added to 250 ml of concentrated hydrochloric acid. The temperature is maintained between 20° to 40° C. and gaseous hydrogen chloride is added over a period of 2 hours. The solution thus obtained is concentrated under vacuum and the residue is extracted with ethyl acetate. The ethyl acetate extract is washed with water, dried over magnesium sulfate and evaporated to give the title compound.

EXAMPLE 8

(−)-α-Amino-3-(azidomethyl)-4-hydroxybenzeneacetic acid

To a solution of (−)-α-amino-3-(chloromethyl)-4-hydroxybenzeneacetic acid (252 mg, 1 mmole) in 4 ml of methyl alcohol is added sodium azide (156 mg, 2.4 mmole). The mixture is stirred at about 40° C. for 15 minutes. After about 10 minutes the title compound begins to precipitate. The mixture is cooled, filtered and the product is washed with a small amount of methyl alcohol and acetone. The title compound is collected (210 mg, 95% yield). M.P.>300°; [α]$_D^{18}$ = −73.03° (c 1.7, water), NMR (DMSO-D$_6$) ppm (δ) 4.22 (s,1), 4.35 (s,2), 6.7–7.5 (superimposed q and s,3).

Anal. calcd for C$_9$H$_{10}$N$_4$O$_3$: N 25.21; Found N, 23.83

EXAMPLE 9

(−)-α-Amino-3-(thiocyanatomethyl)-4-hydroxybenzeneacetic acid

A solution of (−)-α-amino-3-(chloromethyl)-4-hydroxybenzeneacetic acid (0.5 g, 1.98 mmole) and potassium thiocyanate (0.4 g, 4.12 mmole) in 10 ml of methanol is stirred at room temperature for 16 hours. The reaction mixture is filtered to remove the potassium chloride, the filtrate is evaporated and to the residue is added saturated aqueous sodium bicarbonate until the pH is 7. The title compound precipitates as a white powder which is filtered and dried. (1.83 g, 78% yield), NMR (TFA-D+D$_2$O) ppm (δ) 4.1 (s,2), 5.08 (s,1), 6.9–7.3 (m,3).

EXAMPLE 10

(−)-α-Amino-4-hydroxy-3-(methoxymethyl)benzeneacetic acid methyl ester hydrochloride A solution of (−)-α-amino-3-(chloromethyl)-4-hydroxybenzeneacetic acid (1 g, 3.96 mmole) in 10 ml of methanol is refluxed for 30 hours. The solvent is then removed under vacuum and the title compound is isolated in quantitative yield as a hygroscopic powder.

NMR (DMSO-D$_6$+D$_2$O) ppm (δ) 3.40 (s,3), 3.78 (s,3), 4.47 (s,2), 5.20 (s,1), 7.0–7.7 (m,3).

EXAMPLE 11

(−)-α-Amino-4-hydroxy-3-(methoxymethyl)benzeneacetic acid methyl ester (−)-α-Amino-4-hydroxy-3-(methoxymethyl)benzeneacetic acid methyl ester hydrochloride is dissolved in a minimum amount of methanol. To this solution is added methanolic potassium hydroxide until a basic reaction to phenolphthalein is observed. The potassium chloride which precipitates is removed and the solvent is removed under vacuum to give a quantitative yield of the title compound.

NMR (DMSO-D$_6$+D$_2$O) ppm (δ) 3.32 (s,3), 3.64 (s,3), 4.4 (superimposed s,2 and s,1), 6.6–7.3 (m,3).

EXAMPLE 12

(−)-α-Amino-4-hydroxy-3-(methoxymethyl)benzeneacetic acid (−)-α-Amino-4-hydroxy-3-(methoxymethyl)benzeneacetic acid methyl ester is dissolved in aqueous 1 N sodium hydroxide and the solution is stirred at 40°–50° C. for 1 hour. The solution is acidified with 6 N hydrochloric acid to a pH of 7. Evaporation of the solvent gives the title compound in a 90% overall yield.

NMR (D$_2$O) ppm (δ) 3.42 (s,3), 4.56 (s,2), 5.2 (s,1), 7.0–7.5 (m,3).

EXAMPLE 13

(−)-α-Amino-3-[[(aminoiminomethyl)thio]methyl]-4-hydroxybenzeneacetic acid dihydrochloride A solution of (−)-α-amino-3-(chloromethyl)-4-hydroxybenzeneacetic acid (2 g, 8 mmole) and thiourea (0.61 g, 8 mmole) in 10 ml of water is stirred at room temperature for 4 hours. Removal of the solvent by lyophilyzation gives a quantitative yield of the title compound, isolated as its dihydrochloride, [α]$_D^{25}$ = −69.2° (c, 10.4, H$_2$O), NMR (TFA-D) 4.34 (s,2), 5.4 (s,1), 6.8–7.6 (m,3).

EXAMPLE 14

(−)-α-Amino-3-[[(4,5-dihydro-1H-imidazol-2-yl)thio]-methyl]-hydroxybenzeneacetic acid dihydrochloride The title compound as its dihydrochloride is obtained as described in Example 13 when thiourea is replaced by 2-imidazolidinethione. $[\alpha]_D^{25} = -53.41°$ (c, 9.4, H$_2$O), NMR (TFA-D+D$_2$O) ppm ($\delta$) 4.05 (s,4), 4.41 (s,2), 5.16 (s,1), 6.9–7.7 (m,3).

EXAMPLE 15

(−)-α-Amino-4-hydroxy-3-[[(2-methyl-1H-tetrazol-5-yl)thio]-methyl]benzeneacetic acid hydrochloride The title compound as its hydrochloride is obtained by the procedure described in Example 13 when thiourea is replaced by 1-methyl-1H-tetrazol-5-ylthiol.

$[\alpha]_D^{25} = -47.8°$ (c 11.86, H$_2$O), NMR (TFA-D+D$_2$O) 3.96 (s,3), 4.42 (s,2), 5.17 (s,1), 6.8–7.6 (m,3).

EXAMPLE 16

(−)-α-Amino-4-hydroxy-3-(sulfomethyl)benzeneacetic acid monosodium salt

The title compound is obtained after an aqueous solution of sodium sulfite (4 mmole) and (−)-α-amino-3-(chloromethyl)-4-hydroxybenzene (1 g, 4 mmole) in 15 ml of water is refluxed for 3 hours. Lyophilyzation of the solvent gives the title compound as its sodium salt.

NMR (TFA-D+D$_2$O) ppm ($\delta$) 4.1 (s,2), 5.0 (s,1), 6.7–7.4 (m,3).

EXAMPLE 17

(−)-α-Amino-3-[[[[(aminoiminomethyl)amino]iminomethyl]-thio]methyl]-4-hydroxybenzeneacetic acid dihydrochloride A solution of (−)-α-amino-3-(chloromethyl)-4-hydroxybenzeneacetic acid (1 g, 0.4 mmole) and N-(aminoiminomethyl)thiourea (0.47 g, 4 mmole), in 10 ml of water is stirred at room temperature for 4.5 hours. Removal of the solvent by lyophilyzation gives a quantitative yield of the title compound, isolated as its dihydrochloride.

NMR (TFA-D+D$_2$O) ppm ($\delta$) 4.2 (s,2), 5.2 (s,1), 6.8–7.3 (m,3).

EXAMPLE 18

(−)-α-Amino-4-hydroxy-3-(hydroxymethyl)-benezeneacetic acid

To a solution of (−)-α-amino-3-(chloromethyl)-4-hydroxybenzeneacetic acid hydrochloride in water is added saturated aqueous sodium bicarbonate until a pH of 7 is reached. The solution is stirred overnight and is then lyophilyzed to give a quantitative yield of the title compound, combined with 2 equivalents of sodium chloride.

NMR (TFA-D+D$_2$O) ppm ($\delta$) 4.73 (s,2), 5.1 (s,1), 6.9–7.3 (m,3).

EXAMPLE 19

(−)-α-Amino-4-hydroxy-3-[(methylthio)methyl]benzeneacetic acid

To a solution of methanethiol (3 g, 0.04 mmole) in 250 ml of water is added sodium hydroxide (0.04 mole) followed by (−)-α-amino-3-(chloromethyl)-4-hydroxybenzeneacetic acid hydrochloride (5 g, 0.02 mole). The solution obtained is stirred overnight. Removal of the solvent by flash evaporation gives a quantitative yield of the title compound combined with 2 equivalents of sodium chloride.

NMR (TFA-D+D$_2$O) ppm ($\delta$) 2.14 (s,3), 3.78 (s,2), 5.18 (s,1), 6.9–7.3 (m,3).

EXAMPLE 20

(−)-α-Amino-3-[[(ethoxythioxomethyl)thio]methyl]-4-hydroxybenzeneacetic acid

To a solution of (−)-α-amino-3-(chloromethyl)-4-hydroxybenzeneacetic acid hydrochloride (1 g, 0.004 mole) in 20 ml of water is added carbonodithioic acid, O-ethyl ester, potassium salt (1.26 g, 0.08 mole). Within a few minutes a precipitate begins to form. The mixture is stirred at room temperature for 3 hours. The solid precipitate is filtered, washed with water and dried to give 58.3% of the title compound.

$[\alpha]_D^{25} = -81.1°$ (CH$_3$OH, c 5.82), NMR (TFA-D+D$_2$O) ppm ($\delta$) 1.4 (t,3), 4.37 (s,2), 4.6 (q,2), 5.03 (s,2), 6.7–7.5 (m,3).

EXAMPLE 21

3-Azidomethyl-4-hydroxybenzeneacetic acid

A solution of 3-chloromethyl-4-hydroxybenzeneacetic acid (0.1 mole) and sodium azide (0.1 mole) in 250 ml of water is stirred at room temperature for about 16 hours. Removal of the solvent gives the title compound combined with sodium chloride.

Using the procedure described above, the following products are obtained from the thus listed starting materials.

| STARTING MATERIALS | | |
|---|---|---|
| SUBSTITUTED BENZENEACETIC ACIDS | NUCLEOPHILE | PRODUCT |
| α-Hydroxy-3-(chloromethyl)-4-hydroxybenzeneacetic acid | Thiourea | α-Hydroxy-3-[[(aminoiminomethyl)thio]methyl]-4-hydroxybenzeneacetic acid |
| α-Carboxy-3-bromomethyl-4-hydroxybenzeneacetic acid | Potassium methylthiolate | α-Carboxy-4-hydroxy-3-[(methylthio)methyl]benzeneacetic acid |
| α-Sulfo-3-chloromethyl-4-hydroxybenzeneacetic acid | Ammonium cyanate | α-Sulfo-3-cyanatomethyl-4-hydroxybenzeneacetic acid |
| α-(Aminocarbonyl)amino-3-chloromethyl-4-hydroxybenzeneacetic acid | Sodium cyanide | α-(Aminocarbonyl)amino-3-(cyanomethyl)-4-hydroxybenzeneacetic acid |
| α-Amino-3-(chloromethyl)-4-hydroxybenzeneacetic acid | Calcium cyanamide | α-Amido-3-(cyanoamino)methyl]-4-hydroxybenzeneacetic acid |
| α-Amino-3-(chloromethyl)-4-hydroxybenzeneacetic acid | Thiosemicarbazide | α-Amino-3-[[(aminohydrazonomethyl)thio]methyl]-4-hydroxybenzeneacetic acid |
| α-Amino-3-(chloromethyl)-4-hydroxybenzeneacetic acid | Formylthiosemicarbazide | α-Amino-3-[[[amino(formylhydrazono)methyl]thio]methyl]-4- |

-continued

| STARTING MATERIALS | | |
|---|---|---|
| SUBSTITUTED BENZENEACETIC ACIDS | NUCLEOPHILE | PRODUCT |
| α-Amino-3-(chloromethyl)-4-hydroxybenzeneacetic acid | 2-Pyridinethiol | hydroxybenzeneacetic acid α-Amino-4-hydroxy-3-[(2-pyridinylthio)methyl]benzeneacetic acid |
| α-Amino-3-(chloromethyl)-4-hydroxybenzeneacetic acid | 1,3,4-thiadiazol-2-ylthiol | α-Amino-4-hydroxy-3-[(1,3,4-thiadiazol-2-ylthio)methyl]-benzeneacetic acid |
| α-Amino-3-(chloromethyl)-4-hydroxybenzeneacetic acid | 1,3,4-triazol-2-ylthiol | α-Amino-4-hydroxy-3-[(4H-1,2,4-triazol-3-ylthio)methyl]benzeneacetic acid |
| α-Amino-3-(chloromethyl)-4-hydroxybenzeneacetic acid | $Na_2S$ | α-Amino-4-hydroxy-3-(mercaptomethyl)benzeneacetic acid |
| α-Amino-3-(chloromethyl)-4-hydroxybenzeneacetic acid | $NH_2CS_2NH_4$ | α-Amino-3-[[(aminothioxomethyl)-thio]methyl]-4-hydroxybenzeneacetic acid |

EXAMPLE 22

α-(Aminocarbonyl)amino-4-hydroxy-3-methylbenzeneacetic acid

A mixture of α-(aminocarbonyl)amino-3-chloromethyl-4-hydroxybenzeneacetic acid (0.1 mole) and 10% Pd on charcoal (1 g) catalyst in 50 ml of water is subjected to hydrogen gas at a pressure of about 60 pounds/in$^2$ at room temperature for a period of about 16 hours. Removal of the catalyst followed by evaporation of the water gives the title compound.

EXAMPLE 23

The following three procedures may be used to prepare compounds of Formula 1 wherein $R_2$ is tert-butyloxycarbonyl from the corresponding compounds wherein $R_2$ is hydrogen.

PROCEDURE I

To a mixture of an amino acid (40 mmole) and magnesium oxide (80 mmole) in 100 ml of 50% dioxane-water is added t-butyloxycarbonylazide (80 mmole). The mixture is stirred for 16–20 hours at 45°–50° C., it is then cooled, diluted with 400 ml of water and is extracted three times with ethyl acetate. The organic phase is subsequently washed with two portions of 20 ml of 1 N sodium bicarbonate and twice with water. The combined aqueous layers are cooled to 5° C. and acidified to pH 5 with cold 10% aqueous citric acid. The solution obtained is saturated with sodium chloride and is extracted with three portions of 400 ml of ethyl acetate. The organic phase is then dried over sodium sulfate, and the solvent is removed under vacuum. The desired N-tert-butyloxycarbonyl amino acid is thus isolated as an oil or a solid foam.

PROCEDURE II

To a solution of an amino acid (10 mmole) and triethylamine (15 mmole) in 12 ml of 50% water-dioxane is added 2-(tert-butyloxycarbonyloxyimino)-2-phenylacetonitrile (BOC-ON) (11 mmole). The mixture is stirred at room temperature for three hours. To the homogeneous mixture thus obtained, water (15 ml) and ethyl acetate (20 ml) are added. The aqueous phase is separated, washed with ethyl acetate (20 ml), acidified with 5% aqueous citric acid solution and extracted with ethyl acetate. The organic phase is dried and the solvent is removed under vacuum to give the N-tert-butyloxycarbonyl amino acid as an oil or a solid foam.

PROCEDURE III

To a well stirred solution of an amino acid (0.5 mole) and sodium hydroxide (0.5 mole) in 50 ml of water and 100 ml of tert-butanol is added di-tert-butyl dicarbonate [(BOC)$_2$O] (0.55 mole). The mixture is stirred overnight. The turbid solution obtained is diluted with water (250 ml) and is extracted with three portions of pentane (300 ml each). The aqueous phase is cooled, acidified to pH 2-3 with potassium hydrogen sulfate, and is extracted with four 400 ml portions of ethyl acetate. The combined organic phase is dried over anhydrous sodium sulfate, filtered and the solvent removed under reduced pressure. The desired N-tert-butyloxycarbonyl amino acid is thus obtained as an oil or a solid foam.

EXAMPLE 24

(−)-3-(Azidomethyl)-(tert-butyloxycarbonylamino)-4-hydroxybenzeneacetic acid

The title compound is obtained in 55% yield by Procedure I, Example 23, from (−)-α-amino-3-azidomethyl-4-hydroxybenzeneacetic acid.

NMR (CDCl$_3$) ppm (δ) 1.21 (s,9), 1.44 (s,2), 5.05 (broad s,1), 6.5–7.2 (m,3).

EXAMPLE 25

(−)-α-(tert-Butyloxycarbonylamino)-4-hydroxy-3-(methoxymethyl)benzeneacetic acid The title compound is obtained in 72% yield by Procedure I or in 83% yield by Procedure II, Example 23, from (−)-α-amino-4-hydroxy-3-(methoxymethyl)benzeneacetic acid.

NMR (CDCl$_3$) ppm (δ) 1.35 (s,9), 3.40 (s,3), 4.60 (s,2), 5.2 (broad s,1), 6.6–7.5 (m,3).

EXAMPLE 26

α-(tert-Butyloxycarbonylamino)[4-hydroxy-3-[(1-methyl-1H-tetrazol-5-yl)thio]methyl]benzeneacetic acid The title compound is obtained in 30% yield by Procedure III, Example 23, from (−)-α-amino-4-hydroxy-3-[[(1-methyl-1H-tetrazol-5-yl)thio]methyl]benzeneacetic acid.

NMR (CDCl$_3$) ppm (δ) 1.37 (s,9), 3.7 (s,2), 3.8 (s,3), 5.15 (broad s,1), 6.8–7.4 (m,3).

EXAMPLE 27

(—)-(tert-butyloxycarbonylamino)-3-(hydroxymethyl)-4-hydroxybenzeneacetic acid

The title compound is obtained in 76% yield by Procedure II, Example 23, from (—)-α-amino-4-hydroxy-3-(Hydroxymethyl)benzeneacetic acid.

NMR (DMSO-$D_6$+$D_2O$) ppm (δ) 1.4 (s,9), 4.62 (s,2), 5.1 (s,1), 6.8–7.6 (m,3).

EXAMPLE 28

(—)-(tert-Butyloxycarbonylamino)-4-hydroxy-3-[(methylthio)methyl]benzeneacetic acid The title compound is obtained in 81% yield by Procedure III, Example 23, from (—)-α-amino-4-hydroxy-3-[(methylthio)methyl]benzeneacetic acid.

NMR ($CDCl_3$) ppm (δ) 1.4 (s,9), 1.97 (s,3), 3.68 (s,2), 5.1 (broad s,1), 6.6–7.5 (m,3).

EXAMPLE 29

(—)-α-tert-Butyloxycarbonylamino-3-[[(ethoxythioxomethyl)thio]methyl]-4-hydroxybenzeneacetic acid The title compound is obtained in 91.5% yield when prepared according to Procedure III, Example 23, from (—)-α-amino-3-[[(ethoxythioxomethyl)thio]methyl]-4-hydroxybenzeneacetic acid.

NMR ($CDCl_3$) ppm (δ) 1.3–1.5 (superimposed t,3 and s,9), 4.21 (s,2), 4.5 (q,2), 4.96 (broad s,1), 6.4–7.2 (m,3).

EXAMPLE 30

(—)-α-Amino-4-hydroxy-3-[(methylsulfinyl)methyl]-benzeneacetic acid

To an aqueous solution (500 ml) of α-amino-4-hydroxy-3-[(methylthio)methyl]benzeneacetic acid (1 mole) is added sodium metaperiodate (1 mole). The mixture is stirred at room temperature for 5 hours, it is filtered and the filtrate is lyophilyzed to give a quantitative yield of the title compound.

NMR (DMSO-$D_6$+$D_2O$) ppm (δ) 2.65 (s,3), 4.12 (s,2), 4.5 (s,1), 6.8–7.5 (m,3).

EXAMPLE 31

(—)-α-Amino-4-hydroxy-3-[(methylsulfonyl)methyl]-benzeneacetic acid

A solution of α-amino-4-hydroxy-3-[(methylthio)methyl]-benzeneacetic acid (3 g, 8.7 mmole) and 30 ml of 30% hydrogen peroxide in 300 ml of acetic acid is stirred at room temperature for 17 hours. The mixture is filtered and the filtrate is flash concentrated at 35° C. It is mixed with methanol to give a solid which is washed with ether, filtered and dried to give the title compound in 92% yield $[α]_D^{25}$ = —82.07° (dilute HCl, C 9.48).

NMR (TFA-D+$D_2O$) 2.75 (s,3), 4.17 (s,2), 4.8 (s,1), 6.5–7.3 (m,3).

EXAMPLE 32

(—)-α-tert-Butoxycarbonylamino-4-hydroxy-3-[(methylsulfinyl)methyl]benzeneacetic acid The title compound is obtained in 31% yield when prepared from (—)-α-amino-4-hydroxy-3-[(methylsulfinyl)-methyl]benzeneacetic acid according to Procedure III in Example 23.

NMR (DMSO-$D_6$) ppm (δ) 1.4 (s,9), 5.47 (s,3), 4.0 (s,2), 4.98 (m,1), 6.5–7.5 (m,3).

EXAMPLE 33

(—)-α-tert-Butyloxycarbonylamino-4-hydroxy-3-[(methylsulfonyl)methyl]benzeneacetic acid The title compound is obtained in 36% yield when prepared according to Procedure III as described in Example 23 from (—)-α-amino-4-hydroxy-3-[(methylsulfonyl)methyl]-benzeneacetic acid.

NMR ($CDCl_3$) ppm (δ) 1.36 (s,9), 2.67 (s,3), 4.3 (s,2), 5.15 (broad s,1), 6.5–7.4 (m,3).

EXAMPLE 34

6-[[(tert-Butyloxycarbonyl)amino(3-azidomethyl-4-hydroxybenzene)acetyl]amino]-3,3-dimethyl-7-oxo-4-thia-1-azabicyclo[3.2.0]heptane-2-carboxylic acid α-(tert-butyloxycarbonyl)amino(3-azidomethyl-4-hydroxybenzene)acetic acid, 0.3 mole, is dissolved in methylene chloride. Then about 1.5 equivalents of phosphorus pentachloride is added and the mixture is stirred at 0° to 10° C. for about 2 hours. At the end of this time the acid chloride is collected by filtration. α-(tert-Butyloxycarbonyl)amino(3-azidomethyl-4-hydroxybenzene)acetyl chloride (0.1 mole) is added to a solution of 1 equivalent of 6-amino-3,3-dimethyl-7-oxo-4-thia-1-azabicyclo[3.2.0]heptane-2-carboxylic acid in water-tetrahydrofuran containing about 2 equivalents of N,N-dimethylaniline. The mixture is stirred at room temperature for about 3 hours. The tetrahydrofuran is removed under vacuum and the pH of the aqueous phase is adjusted to about 4–5. Upon cooling and diluting with acetonitrile the title compound precipitates.

EXAMPLE 35

7-[[[(3-Chloromethyl)-4-hydroxyphenyl]acetyl]amino]-3-methyl-8-oxo-5-thia-1-azabicyclo[4.2.0]oct-2-ene-2-carboxylic acid 3-(Chloromethyl)-4-hydroxybenzeneacetic acid (1 equivalent) is added to tetrahydrofuran. The reaction mixture is then cooled to —10° C. and 1 equivalent of isobutylchloroformate is added. After 30 minutes at —10° C., 1 equivalent of 7-amino-3-methyl-8-oxo-5-thia-1-azabicyclo[4.2.0]oct-2-ene-2-carboxylic acid in water-tetrahydrofuran containing 1 equivalent of triethylamine is added. After the addition, the reaction temperature is allowed to rise from —10° C. to about 20° C. and maintained at 20° C. for about 60 minutes. Sodium bicarbonate solution is added until the pH is about 4.5 to 5.5. This aqueous solution is then extracted with ethyl acetate. The organic phase is dried over magnesium sulfate and then filtered to remove the magnesium sulfate. Removal of the solvent gives the title compound.

EXAMPLE 36

4-Hydroxy-3-(trifluoromethylthiomethyl)benzeneacetic acid 3-(Chloromethyl)-4-hydroxybenzeneacetic acid (0.05 mole) is added to 150 ml of dimethylformamide. Then 0.15 mole of silver trifluoromethylthiolate is added to the reaction mixture which is stirred at room temperature for about 16 hours. The dimethylformamide is removed at reduced pressure.

The residue is extracted with ethyl acetate. The ethyl acetate extract is dried over magnesium sulfate, the magnesium sulfate is removed by filtration and on removal of the ethyl acetate the title compound is recovered.

We claim:

1. A compound selected from the formula

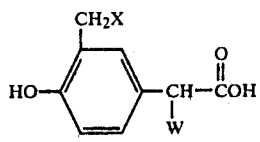

wherein W is hydrogen; hydroxy; SO₃H or —COOR₁ wherein R₁ is selected from hydrogen, phenyl or 5-indanyl, or a 1 to 4 carbon alkyl group; —NHR₂ wherein R₂ is hydrogen, tert-butyloxycarbonyl,

wherein R₃ is hydrogen, a lower alkyl group of from 1 to 4 carbon atoms or a phenyl group; X is an alkoxy group of from 1 to 4 carbon atoms; X is —SCN; or an acceptable salt thereof.

2. A compound of claim 1 wherein W is other than hydrogen or —COOH and is the (—)-isomer or the (+)-isomer.

3. A compound of claim 1 wherein W is hydrogen.
4. A compound of claim 1 wherein W is —COOH.
5. A compound of claim 2 wherein W is hydroxy.
6. A compound of claim 2 wherein W is —SO₃H.
7. A compound of claim 2 wherein W is —NHR₂ wherein R₂ is hydrogen.
8. A compound of claim 2 wherein W is —NHR₂ wherein R₂ is tert-butyloxycarbonyl.
9. A compound of claim 2 wherein W is

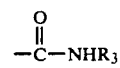

and R₃ is hydrogen, a lower alkyl group of from 1 to 4 carbon atoms or a phenyl group.

* * * * *